(12) United States Patent
Aubert et al.

(10) Patent No.: US 11,896,470 B2
(45) Date of Patent: Feb. 13, 2024

(54) MEDICAL-GRADE ACTUATOR HAVING A MODULAR STRUCTURE AND MEDICAL DEVICE COMPRISING SAME

(71) Applicant: MYOPOWERS MEDICAL TECHNOLOGIES FRANCE SAS, Besancon (FR)

(72) Inventors: Christophe Aubert, Cudrefin (FR); Fabian Kaegi, Lausanne (FR)

(73) Assignee: MYOPOWERS MEDICAL TECHNOLOGIES FRANCE SAS, Besançon (FR)

( * ) Notice: Subject to any disclaimer, the term of this patent is extended or adjusted under 35 U.S.C. 154(b) by 454 days.

(21) Appl. No.: 16/768,075

(22) PCT Filed: Nov. 30, 2017

(86) PCT No.: PCT/IB2017/001637
§ 371 (c)(1),
(2) Date: May 28, 2020

(87) PCT Pub. No.: WO2019/106400
PCT Pub. Date: Jun. 6, 2019

(65) Prior Publication Data
US 2020/0352692 A1   Nov. 12, 2020

(51) Int. Cl.
*A61F 2/00*   (2006.01)
(52) U.S. Cl.
CPC ...... *A61F 2/0036* (2013.01); *A61F 2210/009* (2013.01)

(58) Field of Classification Search
CPC .......................... A61F 2/0036; A61F 2210/009
See application file for complete search history.

(56) References Cited

U.S. PATENT DOCUMENTS

| | | | |
|---|---|---|---|
| 5,503,615 A * | 4/1996 | Goldstein | A61M 60/419 600/16 |
| 6,176,848 B1 * | 1/2001 | Rau | F04D 29/047 600/16 |
| 7,011,621 B2 * | 3/2006 | Sayet | A61F 2/0036 606/151 |

(Continued)

*Primary Examiner* — Thaddeus B Cox
*Assistant Examiner* — Marc D. Honrath
(74) *Attorney, Agent, or Firm* — CRGO Global; Steven M. Greenberg (57) ABSTRACT

Actuator (1) for a medical device (100), comprising an electromotor, a mechanical transmission, and magnetic coupling means arranged for transmitting a mechanical torque from the electromotor to the mechanical transmission when said electromotor is powered by an energy source, wherein said electromotor and a first part of the magnetic coupling means kinematically linked to the electromotor are arranged and hermetically sealed in a first casing module, and wherein said mechanical transmission and a second part of the coupling means kinematically linked to said mechanical transmission are arranged in a second casing module, said first and second casing modules comprising each complementary fastening means such that said first and second casing modules can be removably connected to each other in such a way that said first and second parts of the magnetic coupling means magnetically couple together upon connection of said first and second casing modules.

11 Claims, 3 Drawing Sheets

(56) References Cited

U.S. PATENT DOCUMENTS

2002/0040178 A1    4/2002  Sayet et al.
2007/0050030 A1*  3/2007  Kim .................... A61F 2/4611
                                                        623/17.11
2014/0371855 A1*  12/2014  Clement ................. A61F 2/08
                                                        623/14.13

\* cited by examiner

MEDICAL-GRADE ACTUATOR HAVING A MODULAR STRUCTURE AND MEDICAL DEVICE COMPRISING SAME

CROSS-REFERENCE TO RELATED APPLICATIONS

This application is a § 371 national phase entry of International Application No. PCT/IB2017/001637, filed Nov. 30, 2017, the entirety of which is incorporated herein by reference.

TECHNICAL FIELD

The present invention relates to the field of medical devices. More specifically, the invention relates to a medical grade electromechanical actuator having a modular structure, wherein said actuator comprises a first module hermetically encasing essentially electrical elements of the actuator and a second module encasing essentially mechanical elements of the actuator, said first and second modules being magnetically connectable to each other.

The invention further relates to a medical device comprising such actuator, in particular for actuation of artificial contractile structures such as artificial sphincters, in particular, but not exclusively, for the treatment of urinary incontinence.

BACKGROUND ART

Various forms of artificial contractile structures and associated medical devices have been proposed in the prior art already for the treatment of urinary incontinence. Those existing structures and devices can broadly be classified in two major categories. A first category is the hydraulic/fluidic constricting systems, relying on circulation of a fluid by a pump as actuating means into a fluidic circuit arranged in an artificial sphincter device. A well-known example of such systems is the AUS 800 marketed by American Medical Systems, Inc; but numerous other examples have also been disclosed such as in US2016346071 or US2016135938 recently. A second category is the cable/lead constricting systems, relying on tensile elements such as cables or like being pulled and released by a mechanical actuator to contract and release pressure on a hollow body organ such as the urethra of a patient. The Applicant has been active for long to propose solutions in that second category, such as for example in WO2012000680, WO2013093074 or WO2015117664. In that second category, it is almost compulsory to rely on electromechanical actuators to apply tensile strength on the cables operating the contractile structure.

As such actuators are implanted in the patients' body, it is for obvious safety reasons of the utmost importance to ensure hermetic sealing of the constituting elements of the actuators, in particular of the electrical and electronical elements thereof (direct water ingress in particular). It is likewise important to prevent as much as possible corrosion in any metallic parts of said actuators. However, such hermetic conditioning of the actuators proves difficult due to the almost inevitable ingress of bodily fluids into the actuators at the mechanical connection interface between the cable tensioning elements of the artificial sphincter and the actuators. With time, this may lead to working failure of the actuator, which requires urgent replacement to prevent any risk of patient contamination due to corrosion or leakage from batteries in the actuators.

It is thus an aim of the present invention to propose an improved actuator for medical devices and in particular for medical devices comprising artificial contractile structures for prevention of urinary incontinence.

DISCLOSURE OF THE INVENTION

According to a first object, the invention relates to an actuator for a medical device, in particular for a medical device comprising an artificial contractile structure, as defined in claim 1.

The inventive actuator comprises an electromechanical actuating device comprising an electromotor, a transmission, and magnetic coupling means arranged for transmitting a mechanical torque from the electromotor to the transmission when said electromotor is powered by an energy source.

According to the invention, said electromotor and a first part of the coupling means kinematically linked to the electromotor are arranged and hermetically sealed in a first casing module while said transmission and a second part of the coupling means kinematically linked to said transmission are arranged in a second casing module, said first and second casing modules comprising each complementary fastening means such that said first and second casing modules can be removably connected to each other in such a way that said first and second parts of the magnetic coupling means magnetically couple together upon connection of said first and second casing modules.

The actuator of the invention thus comprises a modular structure, whereby moisture sensitive components of the actuator, such as electrical and electronical components are safely sealed in a first hermetic casing module while non-moisture sensitive components, such as purely mechanical elements are arranged in a second casing module connectable to the first one for them to mechanically couple through complementary parts of magnetic coupling means respectively located in the first and second casing modules.

This provides the advantage to make either the first or the second casing module a "disposable" part of the actuator, which can be removed and changed when necessary in case of dysfunction or else. For example, the mechanical transmission in the second casing module is likely to last much longer than the electronics and batteries received in the first casing part. Replacement of the first casing module and content alone can be performed by simply replacing the subcutaneously implanted first casing module of the actuator. This can even be made in an "ambulatory" setting.

Likewise it may ease replacement at needs of the second casing module and/or any device connected thereto if necessary, for example by laparoscopic surgery, while the first casing module can be left implanted for a much longer period of time due to its hermetic character.

Preferably, the magnetic coupling means comprise a first and a second magnets respectively arranged in the first and second casing modules as first and second parts of the magnetic coupling means, said first and second magnets being coupled respectively to the electromotor and the transmission so as to transmit a mechanical torque from the electromotor to the transmission.

Preferably, a gear head is connected to said electromotor, said gear head holding said first part of the coupling means.

Preferably, the transmission comprises a lead screw cooperating with a nut mounted on said lead screw, said lead screw or said nut being connected on the one hand to said second part of the magnetic coupling means and on the second hand to a driving element for transmitting a driving force to an actuated device through a connector.

Preferably, the actuator comprises a source of energy located in the first casing module to power the electromotor. Still preferably, the source of energy comprises an electrical battery.

Preferably, the actuator comprises an electronic control unit electrically connected to said source of energy and said electromotor, said control unit comprising a microprocessor and a memory onto which a computer program is stored for piloting the electromotor.

Preferably, the control unit comprises wireless transmission means allowing for wireless setting and diagnostics of the control unit and electromotor.

Preferably, the complementary fastening means of said first and second casing modules comprises any of: slide means, magnetic means, snap-fitting means, screwing means, male-female housing means. Preferably, the magnetic coupling means may be sufficient to ensure proper connection between the first and second casing modules.

According to a second object, the present invention further relates to a medical device comprising an actuator as previously described and an artificial contractile device comprising a contractile element and a flexible cable transmission, said flexible cable transmission being connected to the driving element of the transmission in the second casing module.

Preferably, said contractile element is adapted to contract a hollow body organ, said contractile element being in a resting position or in an activated position, the activated position being defined by said contractile element constricting the organ and the resting position being defined by said contractile element not constricting the organ, the actuator being configured to exert tensile strength on the flexible transmission to drive the contractile element from its resting position to its activated position and to release said tensile strength to allow said contractile element to come back to its resting position.

BRIEF DESCRIPTION OF THE DRAWINGS

Further features of the present invention will be described below in connection with the appended drawings, which illustrate.

MODE(S) FOR CARRYING OUT THE INVENTION

Figures 1, 2:
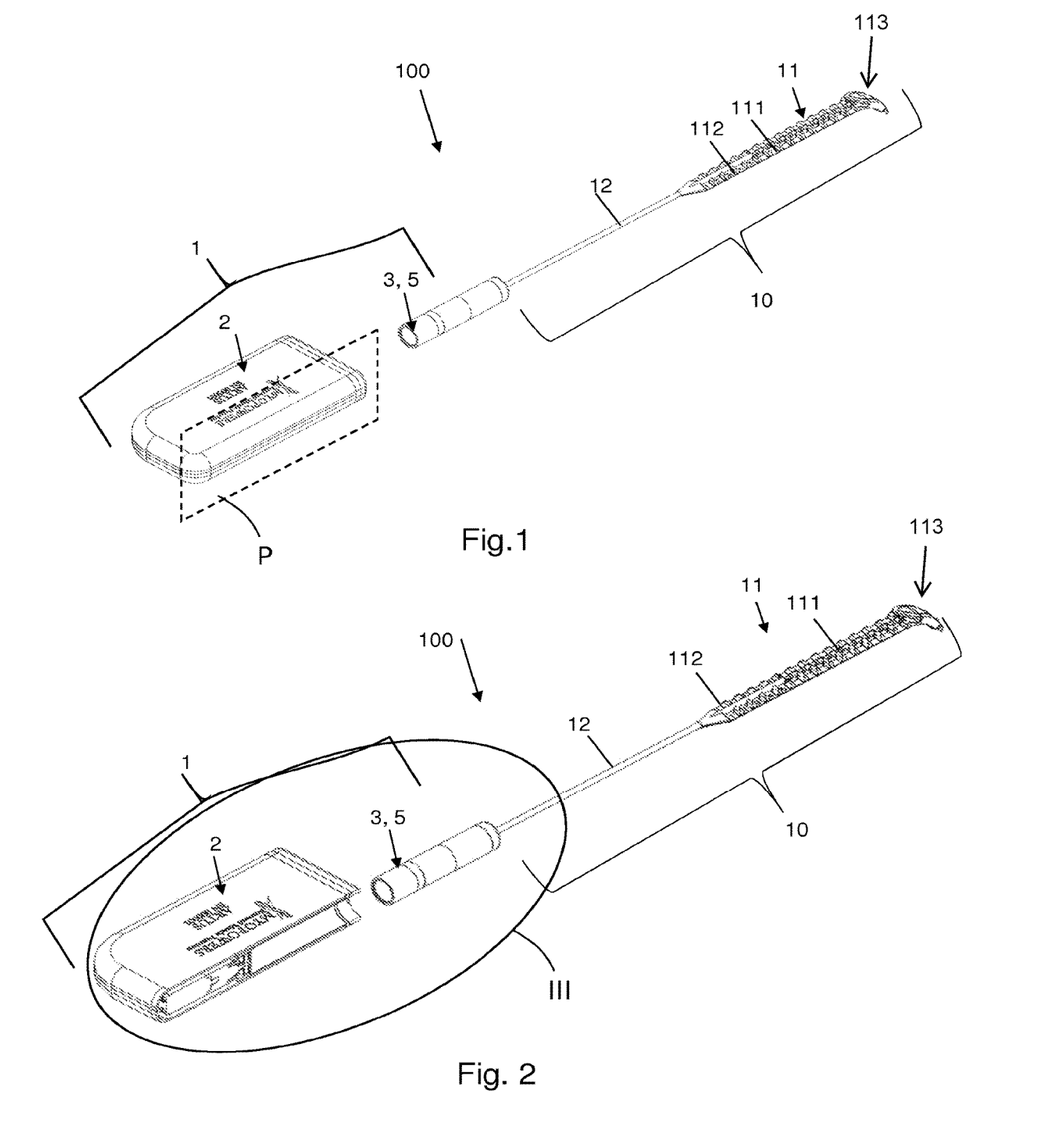
FIG. 1: a schematic, perspective view of a medical device according to the invention comprising an actuator according to the invention comprising am first, main casing module and a second casing module remote from said first module and connected to an artificial contractile structure such as for the treatment of urinary incontinence.
FIG. 2: a similar view as that of FIG. 1 except for a partial cross-section of the first casing module along a longitudinal plan P shown in FIG. 1.
Figure 3:
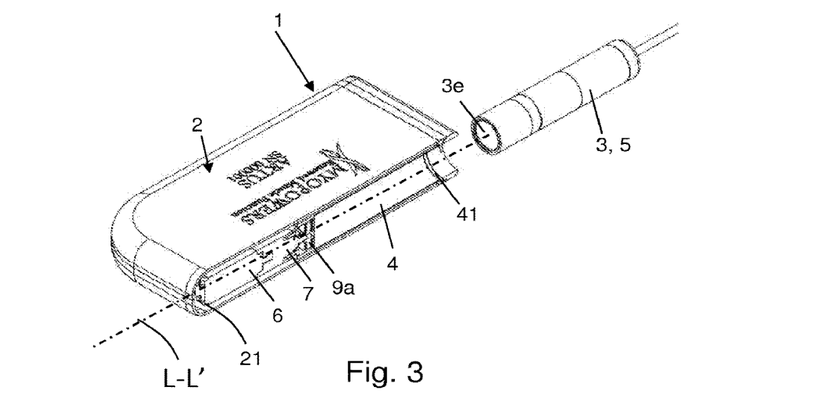
FIG. 3: a schematic, close up perspective view of the actuator of FIG. 2.

FIGS. 1 and 2 represent a medical device 100 according to a preferred embodiment of the present invention. The medical device 100 comprises an artificial contractile device 10 and at least one actuator 1 according to the invention, designed to activate said contractile device 10 in a manner described herein after.

The artificial contractile device 10 comprises at least one contractile element 11 adapted to contract an organ, such as a urethra, when implanted in a patient's body. The artificial contractile device 10 further comprises a flexible transmission 12 for mechanically linking said contractile element 11 to said actuator 1. The contractile element 11 and flexible transmission 12 are advantageously configured such that the contractile element 11 may, thanks to a tensile strength applied by the actuator on the flexible transmission 12, either be in a resting or in an activated position, the activated position being defined with said contractile element 11 constricting an organ such as a urethra about which said contractile element 11 has been formed in a closed loop, and the resting position being defined with said contractile element 11 not constricting the organ.

FIGS. 1 and 2 illustrate a contractile element 11, otherwise known as a cuff, in its open position, i.e. its position before being applied around a hollow body organ. Contractile element 11 comprises a flexible strip or ribbon 111 extending in a longitudinal direction, and constructed e.g. from implant grade silicone elastomer of sufficient Shore hardness, e.g. of between 40 and 80 Shore A, preferably between 50 and 43 Shore A. As non-limiting examples, liquid silicone elastomers from the company Nusil can be used, for instance MED-4843 with shore A hardness 43, MED-4860 with shore A hardness 60, or MED-4850 with shore A hardness 50. Alternatively, polyurethane or other flexible, biocompatible thermoplastic materials may be used instead of, or additionally to, silicone elastomer.

A plurality of transversal reinforcement elements 112 are arranged along flexible strip 4, evenly spaced and numbering in the present example, however the number and the spacing can be chosen according to the needs of the skilled person. Transversal reinforcement elements 112 are aligned substantially perpendicular to the above-mentioned longitudinal direction and show a substantially curved shape, although other forms are also possible. Advantageously, openings are provided between pairs of adjacent transversal reinforcement elements 112. For example formed as slots between some of the transversal reinforcing elements 112. These openings are disposed on the centreline of the contractile element 11 and extend towards its edges. The openings serve to reduce the tensile force required to apply force to the hollow body organ, since less contractile element material needs to be compressed when the contractile element 11 is actuated.

At the distal end of flexible strip 111 is provided a closure 113. The closure 113 is thus arranged so as to be able to form the contractile element 1 into a closed, substantially circular cuff around a hollow body organ by rolling the flexible strip 111 about a said hollow body organ and passing the opposite free end of the artificial contractile device 10 into the closure 113 in order to tighten the contractile element 11 to a desired diameter around it.

When in place about a hollow body organ in its closed position the maximum circumference of contractile element 11 may be for instance 6 cm for implanting around a male urethra, or 11 cm for implanting around the bladder neck in females. However, other maximum circumferences are of course possible. As an example, the width of the flexible strip 111 may be between 7 and 10 mm, however naturally larger and smaller widths are likewise possible. As previously described, the closure 113 is arranged so as to be closed at a number of discrete closing positions, or alternatively may be arranged so that it can be closed at any convenient point along the flexible strip 111.

The flexible transmission 12 extends between said contractile element 11 and actuator 1 as shown in FIGS. 1-4.

Flexible transmission 12 comprises a core of a wire 121 surrounded by a sheath. The sheath comprises an outer sheath 122, e.g. of silicone elastomer, covering a wire coil, which covers the wire 121, broadly following the construction of a Bowden cable. In consequence, pulling or pushing on wire 121 will cause it to move with respect to the sheath. The wire 121 may be e.g. of stainless steel or other metal alloys (e.g. SS 304V, 316L, MP35N, MP35NLT), and may be housed in or coated with an ePTFE or PTFE tube or coating to reduce friction. Additionally, the number and diameter of the strands composing the wire 121 should be chosen to minimise friction, and the wire may also be redrawn so as to make its surface smooth. Alternatively, the wire 121 may be made of titanium, Nitinol, or any other convenient biocompatible metal, or a polymer such as PTFE, Aramid, ultrahigh molecular weight polyethylene (e.g. as sold by Dyneema), or similar. Wire 121 may also be flat or oval in cross-section, and may even be of variable cross-section, e.g. circular within the wire coil, and flat within the contractile element 11. Alternatively, a cable, of either circular or flat cross-section, could be used instead of the wire.

Figure 5:
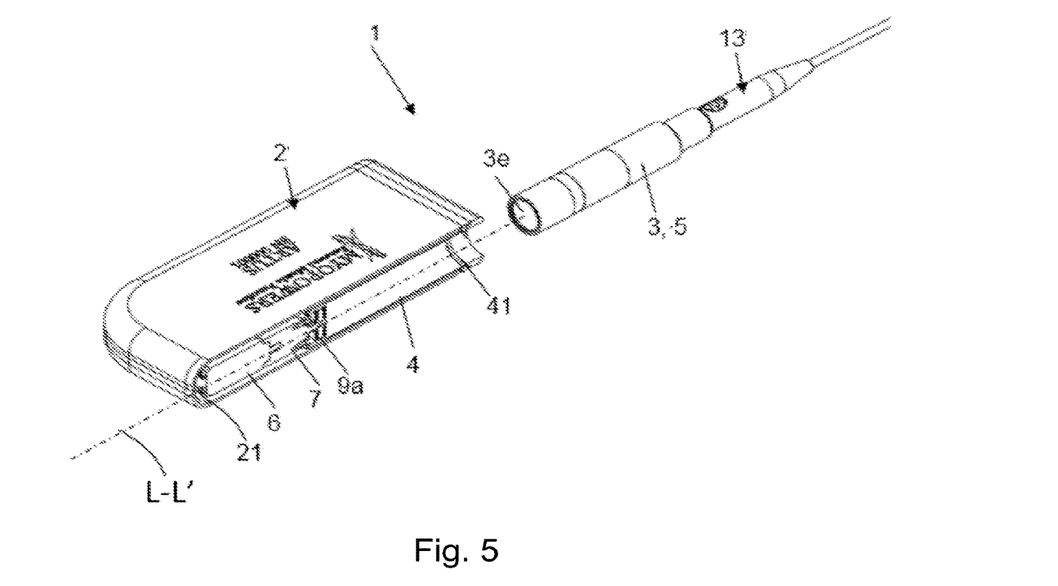
FIG. 5: represents an alternative embodiment of a medical device according to the invention comprising a connector for joining an artificial contractile structure and second casing module of the actuator of the invention.
Figure 6:
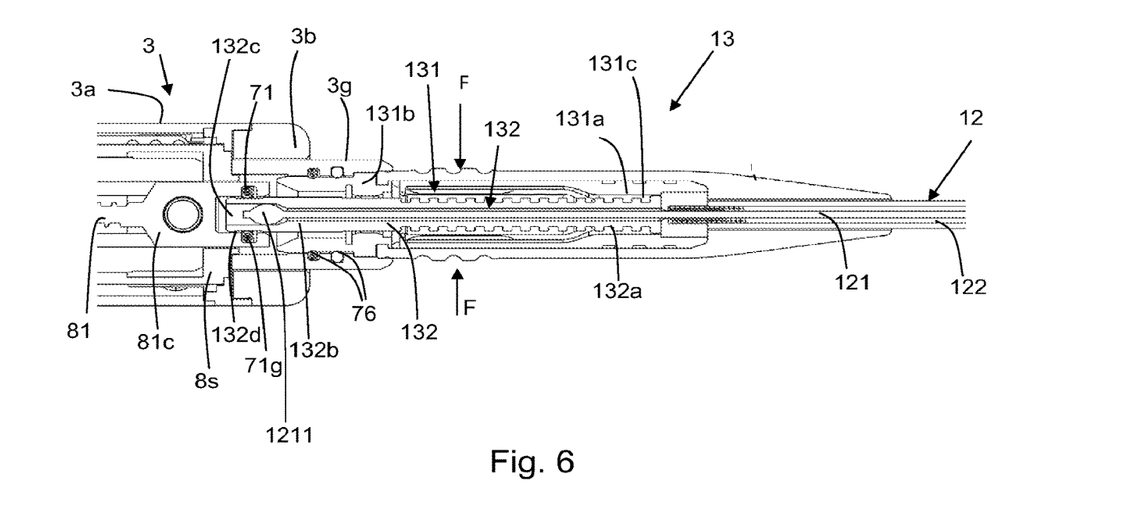
FIG. 6: a schematic cross-sectional view of the connector for the artificial contractile structure of FIGS. 1-2 connected to the second casing module of the actuator of the invention to link the flexible transmission of the artificial contractile structure to the lead-screw of a mechanical transmission arranged in said second casing module.

The actuator 1 comprises at least one electromotor 6 provided with a gearhead 7 and a mechanical transmission 8 connected to the flexible transmission 12 of the contractile element 11 or, as represented in the alternative embodiment of FIGS. 5-6, connectable thereto through connector 13. The actuator 1 is designed to transmit to the contractile element 11 via the flexible transmission 12, and more specifically via its wire 121, a force induced by the electromotor 6.

According to the invention the actuator 1 comprises a first and a second casing modules 2, 3 connectable to each other through complementary fastening means 4, 5. The first casing module 2 is preferably made of biocompatible material, more preferably of titanium, and defines at least an inner chamber 21 wherein the electromotor 6 and its gearhead 7, coupled to the shaft of the electromotor 6 are disposed. An electronic control unit for the electromotor 6 and a source of energy, not visible in the drawings, are also advantageously accommodated in that first chamber 21, which is hermetically sealed and therefore contains elements of the actuator 1, which are the most sensitive to moisture, in particular all electrical and electronical components of the actuator.

The control unit preferably comprises a microprocessor and a memory onto which a computer program is stored for piloting the electromotor. Preferably, the control unit comprises wireless transmission means allowing for wireless setting and diagnostics of the control unit and electromotor. Working parameter adjustments of the control unit can thereby be done after implantation transcutaneously, preferably by a medicinal physician in order to optimize control of volume reduction (such as incontinence leaking). Readjustments can be performed at any time during the life time of the device using a wireless remote control preferably as is known in the art already.

Advantageously, the source of energy is a battery and has a volume less than 20 cm3, preferably less than 15 cm3 and most preferably less than 12 cm3. Such implantable battery is for example a Lithium-Iodine or Lithium-Manganese dioxide primary battery as used in pace-makers or Lithium-Ion or Lithium Polymer rechargeable battery commercialized by GreatBatch, Litronik and others. The energy transfer system that is needed to recharge the battery, is preferably through wireless connection. Such system can comprise a recharge unit, as a belt, comprising an external battery. The patient should wear the recharge unit for a number of hours to recharge the implanted battery. The energy should be transmitted wireless to the implanted battery via appropriate antenna.

The appropriate electromotor 6 is commercialized for example by Maxon Motor AG, Faulhaber or Portescap. Preferably, the gear ratio is comprised between 4 and 64, and preferably between 12 and 64. The lead screw has a pitch comprised between 0.2 mm and 3 mm, preferably between 0.3 mm and 2 mm, and more preferably between 0.4 mm and 1 mm and an effective diameter comprised between 1 mm and 4 mm. Leadscrews with metric threads, for example with a thread angle of 60°, could be used. Preferably, the leadscrew has trapezoidal threads, for example with a thread angle of 30°. This configuration allows to obtain better yield The actuator 1 further comprises a second casing module 3, which is also made of a biocompatible material such as polymer or titanium. However, the second casing module 3 does not need to be hermetically sealed as it contains purely mechanical elements of the actuator 1, i.e. the mechanical transmission 8.

The actuator 1 further comprises magnetic coupling means 9 designed to transmit to the mechanical transmission 8 a torque induced by the electromotor 6. Said magnetic coupling means 9 advantageously comprises at least a first magnet 9a placed on the gearhead 7 of the electromotor 6 in the first casing module 2 and a second magnet 9b placed in the second casing module 3 in a coupling arrangement with said mechanical transmission 8. The magnets 9a, 9b may be of any type but are preferably rare earth magnets, capable of providing a great magnetic coupling and withholding a strong torque with small dimensions of a few millimetres in length, width and thickness. These magnets 9a, 9b may be encapsulated, for example in titanium for higher security and biocompatibility of the actuator 1.

Figure 4:
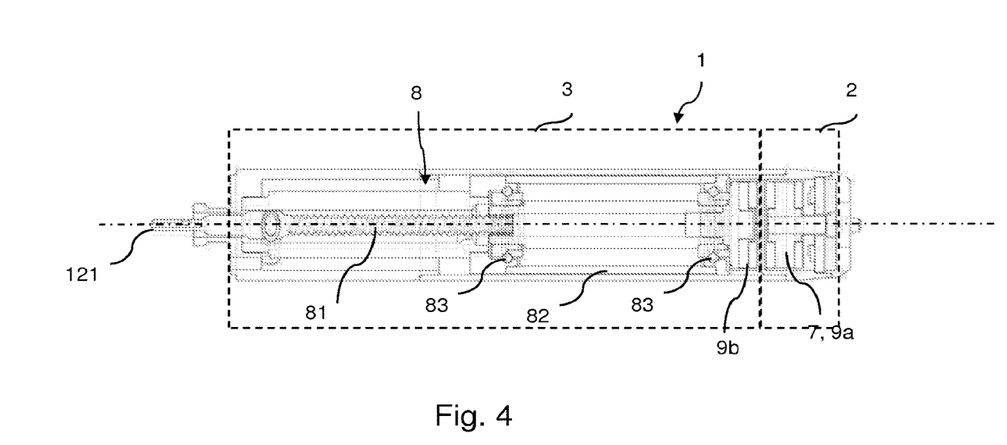
FIG. 4: a schematic cross-sectional view of a screw type actuator known from the prior art, with shadow lined representations of the first casing module and second casing module of the actuator of the present invention.

The mechanical transmission 8 of the actuator 1, remotely disposed into said second casing module 3 advantageously relies on very simple mechanics. FIG. 4 shows a screw type actuator known from the prior art. Dotted rectangles are drawn on top of that figure to represent the respective first casing module 2 and second casing module 3 of the inventive actuator 1 with respect to the various elements they respectively behold.

The mechanical transmission 8 comprises for instance a lead screw 81 and a nut 82 mounted on said lead screw, one of the nut and the lead screw being linked or linkable to the wire 121 of the flexible transmission 12 and the other of the nut and the lead screw holding said second magnet 9b to magnetically couple with said gearhead comprising the first magnet 9a in said first casing module 2 when the second module 3 is fastened thereon through the fastening means 4, 5 as schematically depicted in FIG. 4.

The second casing module 3 thereby only receives and accommodates non moisture sensitive components, which allows for simpler construction of the second module 3, at least without an absolute need for it to be fully hermetic to fluid and moisture ingress, which is particularly difficult to ensure with moving components such as the lead screw and/or nut pulling on the flexible transmission 12. At the same time, this allows for simpler production of the second casing module, which can even be manufactured as a disposable part of the actuator 1. For example, the second casing module 3 may be made of relatively inexpensive biocompatible polymer material, for example two semi-cylindrical halves joined together around the nut 82 and lead screw 81 through any convenient bonding technique (laser sintering or soldering, heat sealing, gluing), and silicon seals may be arranged at the connection end 3c with the flexible transmission 12 to prevent ingress of bodily fluids into the second module casing 3

In a preferred embodiment, the nut is rotatably mounted into the second casing module 3 about a central longitudinal axis L-L' thereof but cannot translate on said axis. The lead screw 81 extends within the nut 82 along said longitudinal axis L-L' of the second casing module 3 and is able to move with respect to said nut along said axis thanks to mutual helical thread engagement between the nut 82 and the lead screw 81. Ball bearings 83 are provided for improving the rotation of the nut 82 and for withstanding the axial forces resulting from the magnetic coupling. Wire 121 from the flexible transmission 12 is preferably attached securely to the tip of the screw 81, which extends through the connection end 3c of the second casing module 3 as shown in FIGS. 1-4 or, as depicted in FIGS. 5-6, to a connector 13, which is itself receivable and linkable to the lead screw 81 in second casing module 3 by a push-fit connection.

Said first magnet 9a secured to the gearhead 7 in the first casing module 2 and said second magnet 9b is secured to the nut 82 in the second casing module 3 are placed face to face against respective contacting walls on the first and second casing modules 2, 3, so as to magnetically couple the gearhead 7 to the nut upon fastening of the second casing module 3 to the first casing module 2 through the fastening means 4, 5. In a simple preferred embodiment represented in FIGS. 1 to 3, the fastening means may comprise a housing tube 4 arranged in the first casing module 2 of the actuator 1, the bottom wall of which housing tube 4 being a flat surface against which the gearhead 7 and first magnet 9a thereon rests. The second casing module 3 then shows a substantially complementary tubular outer shape 5 of chosen diameter to be insertable into the tubular housing 4. Once inserted into said housing 4, the second casing module is sleeved by the first casing module 2, and it magnetically connects to the gearhead 7 at the bottom of the housing 4 by means of the second magnet 9b resting in the second casing module 3 against and end flat wall 3e thereof. In a variant, the casing 3 may not comprise said end wall 3e and encapsulated magnet 9b directly lies at an open end of casing 3 facing, with a gap, the wall of first casing against magnet 9a. in such configuration To prevent body fluid ingress of the first and second casing modules 2, 3 once magnetically couple to each other, an O-ring seal 41 may be provided in a circular notch close the an entry opening of the tubular housing 4, which O-ring seal 41, reduces locally the diameter of the tubular housing 4 such that it provides a friction force against the outer wall of the second casing module 3 when the latter is inserted in the tubular housing 4. Such O-Ring 41 would proves useful in particular to prevent body fluid from being "trapped" between the magnet 9b or and the opposing wall of the 1st casing module 2.

It should be noted that the magnetic coupling between first and second magnets 9a, 9b shall be sufficient to maintain both first and second casing modules 2, 3 together without the need for additional securing means. As a matter of fact, the magnetic coupling is configured to act as a fuse, only allowing disconnection of first and second casing modules 2, 3 in case of unexpected axial pull forces, such as in accidental situations. The magnetic coupling is preferably configured such that the force F required to overcome the magnetic coupling would be in the range of $5N<F<15N$.

Further fastening means may alternatively also be considered instead of male-female means such as tubular housing 4 and complementary tubular outer shape 5 just described. Such fastening means may comprise for example corrugated slides or helical threads allowing for simple adjustment of the second casing module 3 on the first casing module 2 until the end wall 3e comes in abutment against a flat wall of the first casing 2 to magnetically couple the electromotor 6 and gearhead 7 in the first module 2 to the mechanical transmission 8 in the second casing module 3. When this is done, the first magnet 9a rotates with the electromotor 6 when powered by the battery and control unit and transmits rotation to the second magnet 9b that rotates the nut 82. The nut 82 transmits the rotational movement into axial movement of the lead screw 81, which pulls or push on the wire of the flexible transmission 12 to actuate the contractile element 100 from its resting position to its activated position and vice-versa.

FIGS. 5 and 6 illustrate an alternative embodiment for connecting the flexible transmission 12 of the contractile element 11 to the mechanical transmission 8 in the second casing part 3 of the actuator 1 of the invention. This embodiment foresees use of a reversible push-fit connector 13 for linking the wire 121 of said flexible transmission to the lead screw 81 of the mechanical transmission 8 in the second casing part 3.

As shown in FIG. 6, the second casing part 3 comprises a substantially tubular housing 3a inside which the mechanical transmission 8 is mounted. In the FIG. 6, only the farthest connecting end 81c of the lead-screw 81 is visible. This connecting end of the screw 81c extends through a sealing silicon gasket 8s, which may result from an internal lining of the internal cavity defined in housing 3a. A closing ring 3b is fitted over a tubular socket 3g coaxially arranged to the connecting end 81e of the lead screw 81, said socket 3g being compressed on said gasket 8s to ensure substantially liquid tight adjustment of the lead screw, 81, gasket 8s and socket 3g at the connecting end of the housing 3a.

The tubular socket 3g is configured as a female connecting part for the connector 13, in order to guide and retain the latter in engagement with the connecting end 81c of the lead screw 81.

The connector 13 comprises a plug 131 showing a substantially cylindrical body 131a, extending longitudinally within a cavity of a protective shell 132 made of same biocompatible flexible material as the sheath 122 of the flexible transmission 12 preferably, in particular a silicon-based material for example, which can be overmoulded on the plug 131 and integral or glued to the sheath 122. The protective shell 132 may be retained on plug 131 by material insertion into recesses (not shown) arranged on the outer surface of the plug body 131a. A plug head 131b extends outwardly from said body 131a outside the protective shell 132. The plug 131 has an open inner channel or tube 131c extending over the full length thereof, wherein a connecting rod 132 is fitted, said connecting rod comprising a crenelated part 132a housed in the plug's body 131a and a connecting head 132*b* extending through the plug's head 131*b*. Wire 121 is passed in a lumen or capillary in the connecting rod 132 and its knot 1211, is received in an end recess 132*c* in the connecting head 132*b*. Wire 121 are thus fastened to the connecting rod 132, which will mechanically link the transmission 12 to the actuator 3 as will be described herein after, Advantageously, the connecting rod 132 can translate within the plug 131 but that displacement is limited by the toothed configuration of the crenelated part, which engages with inner hooking members radially extending internally from the plug's body 131*a*. These hooking members can be released from the crenelated part by applying pressure as shown by arrows F in FIG. 5.

The head 131*b* of the plug 131 is cylindrical and is a sliding fit within tubular socket 3*g*.

In order to minimise ingress of fluid between connector 13 and the socket tube 3*g*, one or more (in the present example two) sealing rings 76 are provided in corresponding grooves in an inner wall of the socket tube 3*g*, in contact with the outer part of the plug head 131*b*.

Upon insertion of the plug head 131*b* into the socket 3*g* the connecting head 132*b* attaches to a distal extremity 81*c* of the lead-screw 81 by any convenient attachment. In the illustrated embodiment, a first toroidal spring 71 held within a corresponding first annular groove 71*g* in the distal extremity 81*c* of the lead-screw 81 cooperates in a corresponding groove 132*d* arranged on the outer surface of the connecting head 132*b*. As an alternative, an O-ring may be used instead of a toroidal spring. Upon insertion of the connecting head 132*b* in the distal extremity 81*c* of the lead-screw 81, the toroidal spring 71 clips into the annular groove 132*d* so as to retain the connecting head 132*b* and plug 131 upon the distal extremity of the lead-screw and to transmit force and movement thereto. In this sense, the toroidal spring provides a kinematic link between the connecting rod 132 and the distal extremity of the lead screw 81. As a variation, the position of the two annular grooves 71*g*, 132*d* can be inverted if desired, the toroidal spring 71 thereby being supported in the connecting head 132*b* and clipping into the groove in the distal extremity 81*c* of the lead screw 81.

The wire 121 of the flexible transmission is held to the connecting rod 132 of the connector 13 by an anchoring knot 1211 which is secured to a plug 131.

With this configuration, it is particularly easy to connect the artificial contractile device 10 to the actuator 1 by simple reversible push fit insertion of the connector 13 into the socket 3*g* of the second casing module, the connecting rod 132 anchoring the wire 121 of the flexible transmission 12 direction engaging into the lead-screw 81 of the mechanical transmission 8 of the actuator accommodated in said second casing. This provides ultimate ease of implantation for a surgeon, who can easily implant separately the artificial contractile device 10, for example by laparoscopy surgery and adjust it on an organ while the flexible transmission 12 remains free from connection to the actuator 1, which can be implanted remotely. Once the artificial contractile device 10 and actuator are set in place, the surgeon just needs plugging the connector 13 into the second casing module 3 of the actuator, and then plug that one into the first casing 2 in the housing foreseen to that end.

More importantly, it is now with the actuator 1 of the invention possible to change the second casing part 2 and mechanical transmission separately from both the electronic parts of the actuator in the first casing module, which is hermetically sealed, and from the contractile device 1. This provides lower and safer maintenance procedures for both patients and practitioners, at lower costs as maintenance operations are shorter and only part of the actuator 1 needs changing instead of removing and replacing the whole actuator as in the prior art solutions.

Although the invention has been described in terms of specific embodiments, variations thereto are possible without departing from the scope of the invention as defined in the appended claims.

The invention claimed is:

1. An actuator for a medical device, comprising an electromotor, a mechanical transmission, and magnetic coupling means arranged for transmitting a mechanical torque from the electromotor to the mechanical transmission when said electromotor is powered by an energy source, wherein said electromotor and a first part of the magnetic coupling means kinematically linked to the electromotor are encased and hermetically sealed in a first casing module, and wherein said mechanical transmission and a second part of the magnetic coupling means kinematically linked to said mechanical transmission are encased in a second casing module which is separate from the first casing module, said first and second casing modules comprising each complementary fastening means such that said first and second casing modules can be removably connected to each other in such a way that said first and second parts of the magnetic coupling means magnetically couple together upon connection of said first and second casing modules.

2. The actuator according to claim 1, wherein the magnetic coupling means comprises first and a second magnets respectively arranged in the first and second casing modules as first and second parts of the magnetic coupling means, said first and second magnets being coupled respectively to the electromotor and the mechanical transmission so as to transmit the mechanical torque from the electromotor to the mechanical transmission.

3. The actuator according to claim 1, wherein a gear head is connected to said electromotor, said gear head holding said first part of the magnetic coupling means.

4. The actuator according to claim 1, wherein the mechanical transmission comprises a lead screw cooperating with a nut mounted on said lead screw, said lead screw or said nut being connected to said second part of the magnetic coupling means and on to a driving element for transmitting a driving force to an actuated device.

5. The actuator according to claim 1, wherein the energy source is located in the first casing module to power the electromotor.

6. The actuator according to claim 5, wherein the energy source comprises an electrical battery.

7. The actuator according to claim 1, further comprising an electronic control unit electrically connected to said energy source and said electromotor, said control unit comprising a microprocessor and a memory onto which a computer program is stored for piloting the electromotor.

8. The actuator according to claim 7, wherein the control unit comprises wireless transmission means allowing for wireless setting and diagnostics of the control unit and electromotor.

9. The actuator according to claim 1, wherein complementary fastening means of said first and second casing modules are provided, which the complementary fastening means comprises fastening means selected from the group consisting of slide means, magnetic means, snap-fitting means, screwing means, and male-female housing means.

10. A medical device comprising an actuator and an artificial contractile device comprising a contractile element and a flexible transmission, said actuator comprising an electromotor, a mechanical transmission, and magnetic coupling means arranged for transmitting a mechanical torque from the electromotor to the mechanical transmission when said electromotor is powered by an energy source, wherein said electromotor and a first part of the magnetic coupling means kinematically linked to the electromotor are encased and hermetically sealed in a first casing module, and wherein said mechanical transmission and a second part of the magnetic coupling means kinematically linked to said mechanical transmission are encased in a second casing module which is separate from the first casing module, said first and second casing modules comprising each complementary fastening means such that said first and second casing modules can be removably connected to each other in such a way that said first and second parts of the magnetic coupling means magnetically couple together upon connection of said first and second casing module, said flexible transmission being connectable to the mechanical transmission in the second casing module of the actuator.

11. The medical device according to claim 10, wherein said contractile element is adapted to contract a hollow body organ, said contractile element being in a resting position or in an activated position, the activated position being defined by said contractile element constricting the organ and the resting position being defined by said contractile element not constricting the organ, the actuator being configured to exert tensile strength on the flexible transmission to drive the contractile element from its resting position to its activated position and to release said tensile strength to allow said contractile element to come back to its resting position.

* * * * *